United States Patent
Wisweh

(10) Patent No.: US 9,704,035 B2
(45) Date of Patent: Jul. 11, 2017

(54) APPARATUS FOR OPTICAL COHERENCE TOMOGRAPHY OF AN EYE AND METHOD FOR OPTICAL COHERENCE TOMOGRAPHY OF AN EYE

(71) Applicant: Novartis AG, Basel (CH)

(72) Inventor: Henning Wisweh, Erlangen (DE)

(73) Assignee: Novartis AG (CH)

( * ) Notice: Subject to any disclaimer, the term of this patent is extended or adjusted under 35 U.S.C. 154(b) by 219 days.

(21) Appl. No.: 14/441,724

(22) PCT Filed: May 29, 2013

(86) PCT No.: PCT/EP2013/061061
§ 371 (c)(1),
(2) Date: May 8, 2015

(87) PCT Pub. No.: WO2014/191031
PCT Pub. Date: Dec. 4, 2014

(65) Prior Publication Data
US 2015/0294147 A1    Oct. 15, 2015

(51) Int. Cl.
G06K 9/00    (2006.01)
A61B 3/10    (2006.01)

(52) U.S. Cl.
CPC .......... *G06K 9/00604* (2013.01); *A61B 3/102* (2013.01); *G06K 9/0061* (2013.01)

(58) Field of Classification Search
CPC combination set(s) only.
See application file for complete search history.

(56) References Cited

U.S. PATENT DOCUMENTS

| | | | |
|---|---|---|---|
| 5,644,642 A | 7/1997 | Kirschbaum | |
| 7,418,115 B2 * | 8/2008 | Northcott | A61B 3/1216 351/220 |
| 8,085,408 B2 * | 12/2011 | Everett | A61B 3/102 356/497 |
| 8,363,783 B2 * | 1/2013 | Gertner | A61B 3/113 351/206 |
| 8,630,388 B2 * | 1/2014 | Gertner | A61B 3/113 378/65 |
| 8,705,048 B2 * | 4/2014 | Everett | A61B 3/102 356/497 |
| 2007/0291277 A1 * | 12/2007 | Everett | A61B 3/102 356/497 |
| 2008/0055543 A1 | 3/2008 | Meyer et al. | |
| 2011/0007321 A1 * | 1/2011 | Everett | A61B 3/102 356/479 |
| 2011/0267340 A1 | 11/2011 | Kraus et al. | |
| 2011/0286003 A1 * | 11/2011 | Ono | A61B 3/102 356/495 |
| 2012/0026464 A1 * | 2/2012 | Berger | A61B 3/102 351/206 |
| 2012/0083667 A1 | 4/2012 | Isogai | |

(Continued)

FOREIGN PATENT DOCUMENTS

| | | |
|---|---|---|
| JP | 2000-312664 | 11/2000 |
| JP | 2008-104628 | 5/2008 |

(Continued)

*Primary Examiner* — Anand Bhatnagar

(57) ABSTRACT

An apparatus and a method for optical coherence tomography (OCT) of an eye are provided. The apparatus comprises a camera system, an OCT image-acquisition unit, and a control unit.

13 Claims, 5 Drawing Sheets

(56) References Cited

U.S. PATENT DOCUMENTS

Figure 1:
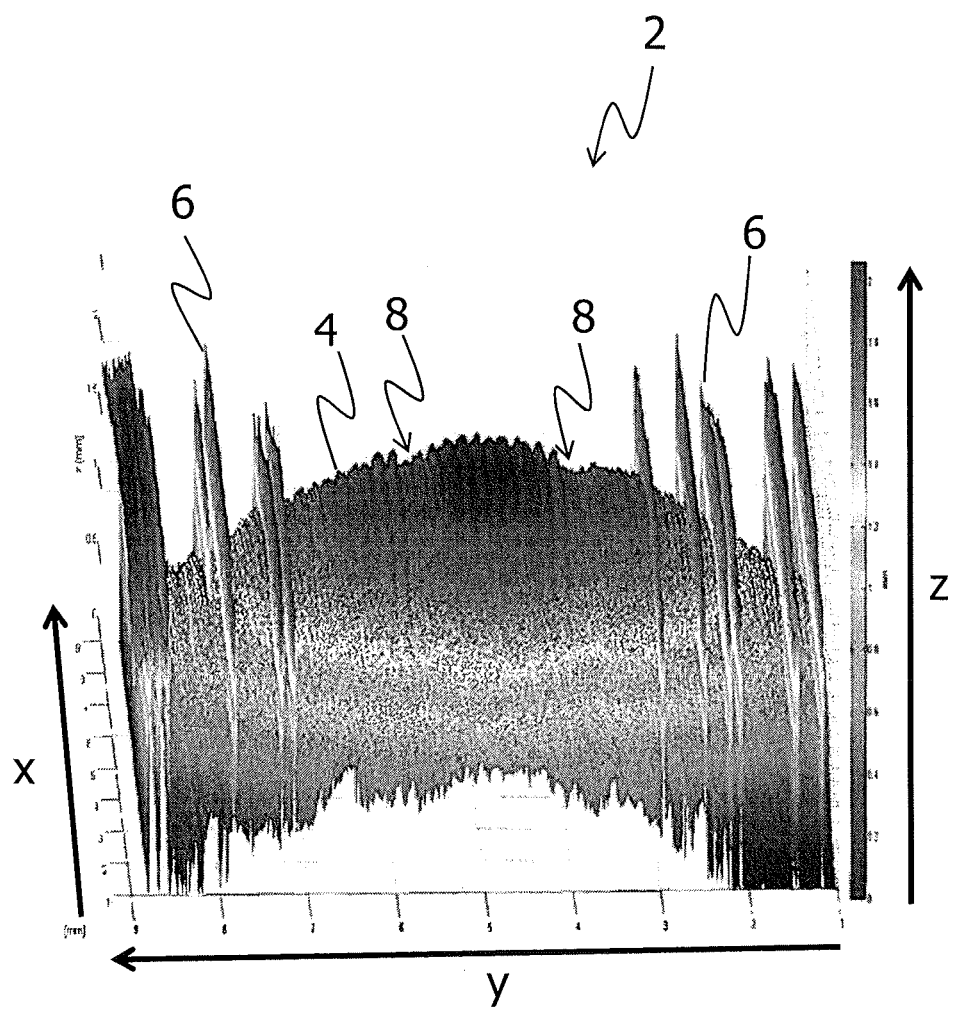

| | | | | |
|---|---|---|---|---|
| 2012/0140174 A1* | 6/2012 | Hee | ............ | A61B 3/0025 |
| | | | | 351/206 |
| 2012/0200824 A1* | 8/2012 | Satake | ............ | A61B 3/102 |
| | | | | 351/206 |
| 2012/0229762 A1* | 9/2012 | Makihira | ............ | A61B 3/102 |
| | | | | 351/206 |
| 2012/0274783 A1 | 11/2012 | Ko et al. | | |
| 2013/0141696 A1* | 6/2013 | Gertner | ............ | A61B 3/113 |
| | | | | 351/206 |
| 2014/0192324 A1* | 7/2014 | Straub | ............ | A61B 3/102 |
| | | | | 351/206 |

FOREIGN PATENT DOCUMENTS

| | | |
|---|---|---|
| JP | 2008104628 A | 5/2008 |
| JP | 2009-142313 | 7/2009 |
| JP | 2012-161427 | 8/2012 |

* cited by examiner

APPARATUS FOR OPTICAL COHERENCE TOMOGRAPHY OF AN EYE AND METHOD FOR OPTICAL COHERENCE TOMOGRAPHY OF AN EYE

CROSS REFERENCE TO RELATED APPLICATIONS

This application is a section 371 national stage phase of International Application No. PCT/EP2013/061061, filed 29 May 2013, titled "APPARATUS FOR OPTICAL COHERENCE TOMOGRAPHYOF AN EYE AND METHOD FOR OPTICAL COHERENCE TOMOGRAPHY OF AN EYE," which is hereby incorporated by reference in its entirety.

TECHNICAL FIELD

The present disclosure generally relates to optical coherence tomography. More specifically, embodiments of the present disclosure relate to an apparatus for optical coherence tomography of an eye and a method for optical coherence tomography of an eye.

BACKGROUND

For creating a three-dimensional (3D) tomogram of an eye with the aid of optical coherence tomography (OCT), it is conventional to record a plurality of OCT images arranged in lines (such as A-scans) and/or layers (such as B-scans) with respect to one another within a volume of the eye to be scanned and to register these images subsequently with respect to one another to form a tomogram.

However, during the capture of the multiple OCT images the eye may undergo movements. In this case, after 3D registration the resulting 3D tomogram shows movement induced artifacts. These artifacts reduce the quality of the 3D tomogram as, for example, the geometry, the contour or the height profile of the eye or of single parts of it, such as the cornea, are reproduced in the tomogram in a less qualitative way.

SUMMARY

There is a need to provide an apparatus for optical coherence tomography of an eye and a method for optical coherence tomography of an eye that enable tomograms of improved quality.

An apparatus for OCT of an eye comprises a camera system configured to capture time-resolved camera images of the eye and an OCT image-acquisition unit configured to acquire time-resolved OCT images of the eye. A measuring axis of the OCT image-acquisition unit and a measuring axis of the camera system are aligned along a common measuring axis of the apparatus using a beam splitter. The apparatus further comprises a control unit configured to determine, from the time-resolved camera images, time-resolved movement data representing a movement of the eye relative to the measuring axis of the apparatus. The control unit is also configured to transform at least a fraction of the OCT images on basis of the movement data and to generate a tomogram from the OCT images, for example, from the transformed OCT images.

In other words, the apparatus may employ a camera system for imaging the eye in a time-resolved manner such that the control unit can extract movement data out of the camera images that allow to specify a movement of the eye, for example, to decide, whether at all and, if yes, how the eye moves. Thus, the time-resolved movement data may allow the reconstruction of the spatial position and orientation of the eye in a time-resolved manner. The spatial position and orientation of the eye may refer to the measuring axis of the apparatus and thus to the position and orientation of the apparatus. From the movement data the control unit may interpolate a spatial position and/or orientation of the eye in a time-resolved manner, for example, even for times between two subsequent captures of camera images. Therefore, the camera system may be regarded as an eye tracker. Correspondingly, the movement data may be regarded as eye tracking data.

As the OCT images of the eye are also acquired in a time-resolved manner, each of the OCT images can be associated with a corresponding spatial position and orientation of the eye. Thus, the OCT images can be processed on the basis of the movement data. For example, OCT images that would lead to a movement induced artifact in the tomogram may be (pixel-wise) transformed by means of linear transformation functions, such as rotations or translations, such that the movement of the eye is compensated. The apparatus may be adapted such that the OCT images may be positioned and/or orientated (i.e. registered) with respect to each other. This allows the generation of tomograms without movement artifacts and thus of improved quality. As long as the OCT-image acquisition may be synchronized with the acquisition of the movement data or as far as the OCT-image data and the movement data may be correlated in time with respect to each other, it is of minor concern how the OCT-images are acquired or how the specific scan algorithm looks like.

The measuring axis of the camera system may be the optical axis of one or all cameras comprised in the camera system. The measuring axis of the OCT image-acquisition unit may be the propagation direction of the sample light beam in the sample arm of the OCT image-acquisition unit. The common measuring axis of the apparatus may be the optical axis defined by a scanning objective of the OCT image-acquisition unit. The beam splitter may be a cube, plate, pellicle or a semi-transparent mirror or a band pass mirror that only reflects or transmits a frequency band, in which the frequency of the light of the OCT acquisition unit falls. The beam splitter may be coated with dichroic layers. The camera system may image the eye through the scanning objective of the OCT image-acquisition unit. From the movement data, the control unit may interpolate spatial position and orientation of the eye in a time-resolved manner, for example, even for times between two subsequent captures of camera images. An OCT image may represent a single line scan (A-scan), a layer scan (B-scan) comprising multiple line scans or a volume scan comprising multiple B-scans. A single OCT image may be acquired so fast that during the acquisition time substantially no artifact emerges in the OCT image. Time-resolved movement data may be understood as time-resolved spatial position data. From the time-resolved spatial position data time-resolved movement data (and vice versa) can be calculated, e.g., by using the control unit.

The apparatus may further comprise at least two spot lights being configured to illuminate the cornea of the eye such that the time-resolved camera images comprise for each spot light a light mark. The light mark may be a reflection from an eye surface, e.g., the cornea, and may result in a Purkinje reflex or a Purkinje image. To this end, the spot lights may be arranged laterally shifted from the measuring axis of the apparatus in a fixed manner. The spot light illumination allows a time-resolved spatial tracking of (e.g., the centers of) the light marks shown in the camera images. For this purpose, the control unit may be configured to determine as movement data a time-resolved spatial position of the at least two light marks. From the movement data, the distance between the positions of the two light marks can be calculated, e.g., using the control unit. This distance changes with an axial translation of the eye relative to the apparatus. 'Axial' may correspond to the z-coordinate along the measuring axis of the apparatus. The control unit may be calibrated such that for any spatial position of the light marks and/or any spatial distance between the position of the at least two light marks a corresponding axial (z) translation of the eye relative to the apparatus may be assigned. This allows a precise time-resolved axial (z) tracking of the position and/or movement of the eye and thus a correction of the OCT images free from z-translations induced artifacts.

Additionally or alternatively, the apparatus may comprise a plurality of spot lights arranged in a spot light geometrical pattern. The spot light geometrical pattern may be a circular, a circular-like, a rectangular, a rectangular-like, a star or a star-like pattern. The spot lights may be configured to illuminate the cornea of the eye such that the time-resolved camera images comprise a plurality of light marks in a light mark geometrical pattern, such as a circular, a circular-like, a rectangular, a rectangular-like, a star or a star-like pattern. The control unit may be configured to determine, as movement data, a time-resolved spatial size of a geometrical pattern, e.g., a circular, a circular-like, a rectangular, a rectangular-like, a star and/or a star-like pattern fitted to the plurality of light marks. For example, in case of a circle, the time-resolved spatial size may be represented by a diameter of the fitted circle. This may be considered to correspond to a simultaneous determining of distances between positions of two light marks for various different pairs of light marks representing an inherent averaging. The control unit may be calibrated such that for each spatial size of the geometrical pattern fitted to the light marks a corresponding axial (z) translation of the eye relative to the apparatus may be assigned. This may allow a more precise time-resolved axial (z) tracking of the position and/or movement of the eye and thus an improved correction of the OCT images free from z-translations induced artifacts.

The apparatus may comprise a cornea contour determining unit being configured to determine curvature values representing the curvature of the outer cornea surface of the eye. This may allow the determining of the curvature along the meridians of the outer surface of the cornea and thus a more precise calibration of the control unit for assigning the axial (z) translation of the eye relative to the apparatus. For example, the cornea contour determining unit may be a component of the apparatus separate from the camera system and the OCT image acquisition unit.

Alternatively or additionally to the foregoing, the control unit may be configured to determine curvature values from the OCT images, the curvature values representing the curvature of the outer cornea surface of the eye.

The spot lights may be light emitting diodes (LEDs, OLEDs, etc.). The camera system may comprise a separate camera, such as a video camera, for capturing the camera images showing the light marks.

Alternatively or additionally, the control unit may be configured to determine, as movement data, a time-resolved position of a reference point being the center of a geometrical pattern, e.g., a circle and/or an ellipse fitted to the pupil of the eye and/or to an outer edge of the iris of the eye and/or the center of a geometrical pattern, such as a circular, a circular-like, a rectangular, a rectangular-like, a star or a star-like pattern, fitted to the light marks. Thus, for example, a tilting of the eye relative to the measuring axis may be detected by a shifting of the center of the geometrical pattern fitted to the pupil of the eye and/or to an outer edge of the iris of the eye relative to the center of the geometrical pattern fitted to the light marks. This may allow a time-resolved lateral (x, y) tracking of the position and/or movement of the eye and thus a correction of the OCT images free from lateral (x, y) translations induced artifacts. 'Lateral' may correspond to the x- and/or y-coordinate(s) in a direction perpendicular to the measuring axis of the apparatus. In particular, the apparatus may be calibrated such that for each said shifting of the center of the geometrical pattern fitted to the pupil of the eye and/or to an outer edge of the iris of the eye relative to the center of the geometrical pattern fitted to the light marks a specific tilting angle of the eye relative to the measuring axis can be calculated. Moreover, the apparatus may be adapted to register the OCT images with respect to each other on basis of said calculated tilting angle.

The camera system may comprise a separate camera, such as a video camera, for capturing the camera images showing the pupil, the limbus and/or the iris of the eye.

Alternatively or additionally, the control unit may be configured to determine, as movement data, a time-resolved position of an eye feature being an extended feature of the iris of the eye and/or of a vessel structure in the sclera of the eye. This may allow a time-resolved rotational (cyclotorsional) tracking of the position and/or movement of the eye and thus a correction of the OCT images free from rotations (cyclotorsions) induced artifacts.

The camera system may comprise a separate camera, such as a video camera, for capturing the camera images showing the extended feature of the iris and/or of a vessel structure in the sclera.

The camera system may only comprise a single camera for capturing camera images showing the light marks, for capturing the camera images showing the pupil, the limbus and/or the iris of the eye, and for capturing the camera images showing the extended feature of the iris and/or of a vessel structure in the sclera. This may allow designing a compact and light apparatus.

The camera system may be configured to capture time-resolved camera images with a camera imaging rate. The OCT image-acquisition unit may be configured to acquire time-resolved OCT images with an OCT imaging rate. The control unit may be configured to control the camera imaging rate and/or the OCT imaging rate.

The camera imaging rate may substantially equal the OCT imaging rate. For example, the camera imaging rate and the OCT imaging rate may be synchronized to one another. This allows assigning a single camera image to each OCT image and thus a time-adapted correction of the OCT images free from movement artifacts.

Alternatively, the camera imaging rate may be lower than the OCT imaging rate. This may allow assigning a single camera image to multiple different OCT images, thus a less time-consuming determining of the movement data and therefore a faster generation of tomograms.

Still alternatively, the camera imaging rate may be higher than the OCT imaging rate. This may allow assigning multiple camera images to each OCT image enabling, for example, a highly time-resolved correction of the OCT images on an A-scan basis when each OCT scan comprises several A-scans.

A method for optical coherence tomography (OCT) of an eye comprises the steps of:

capturing time-resolved camera images of the eye using a camera system, acquiring time-resolved OCT images of the eye using an OCT image-acquisition unit, wherein a measuring axis of the OCT image-acquisition unit and a measuring axis of the camera system are aligned along a common measuring axis, determining, from the time-resolved camera images, time-resolved movement data representing a movement of the eye relative to the measuring axis using a control unit, transforming at least a fraction of the OCT images on basis of the movement data using the control unit, and generating a tomogram from the OCT images, for example, from the transformed OCT images, using the control unit.

The common measuring axis may be a common measuring axis of the apparatus for performing the method.

To the extent that a method or individual steps of a method for optical coherence tomography is/are described in this description, the method or individual steps of the method can be executed by an appropriately configured apparatus or components of the apparatus. Analogous remarks apply to the elucidation of the mode of operation of an apparatus that executes method steps. To this extent, apparatus features and method features of this description may be considered equivalent.

Above, the apparatus for optical coherence tomography and/or the method for optical coherence tomography is/are described with respect to an eye. However, the apparatus and/or the method may also be employed for optical coherence tomography of any other sample.

DETAILED DESCRIPTION

Figure 2:
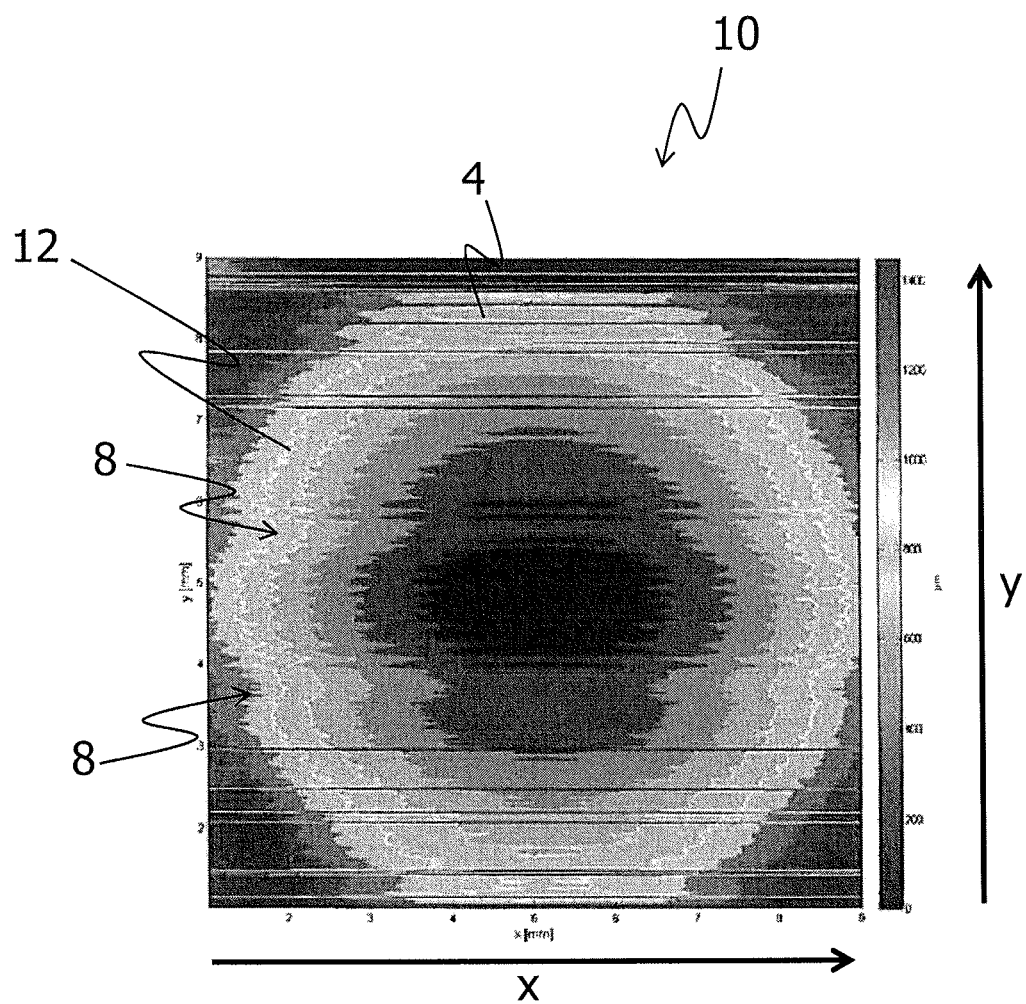
Figure 3:
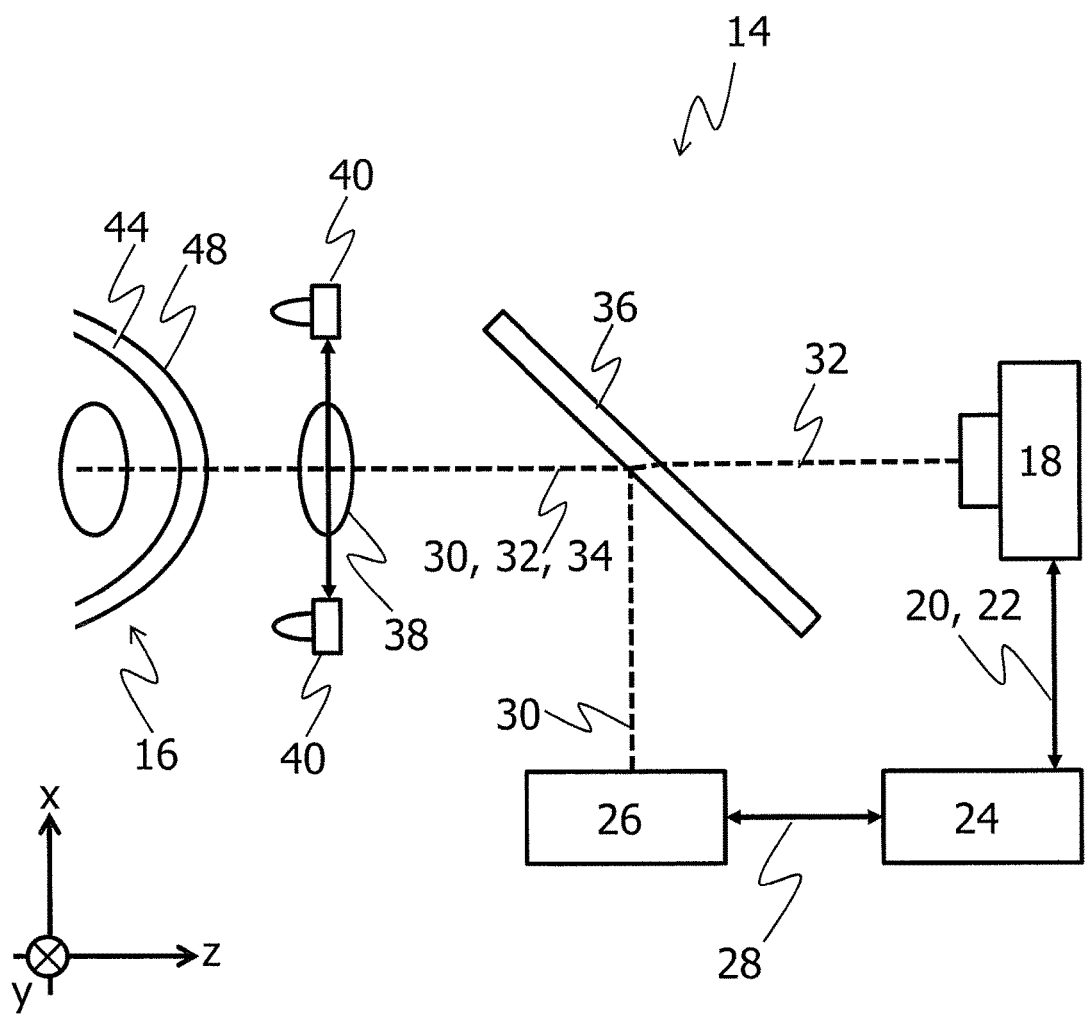
Figure 4:
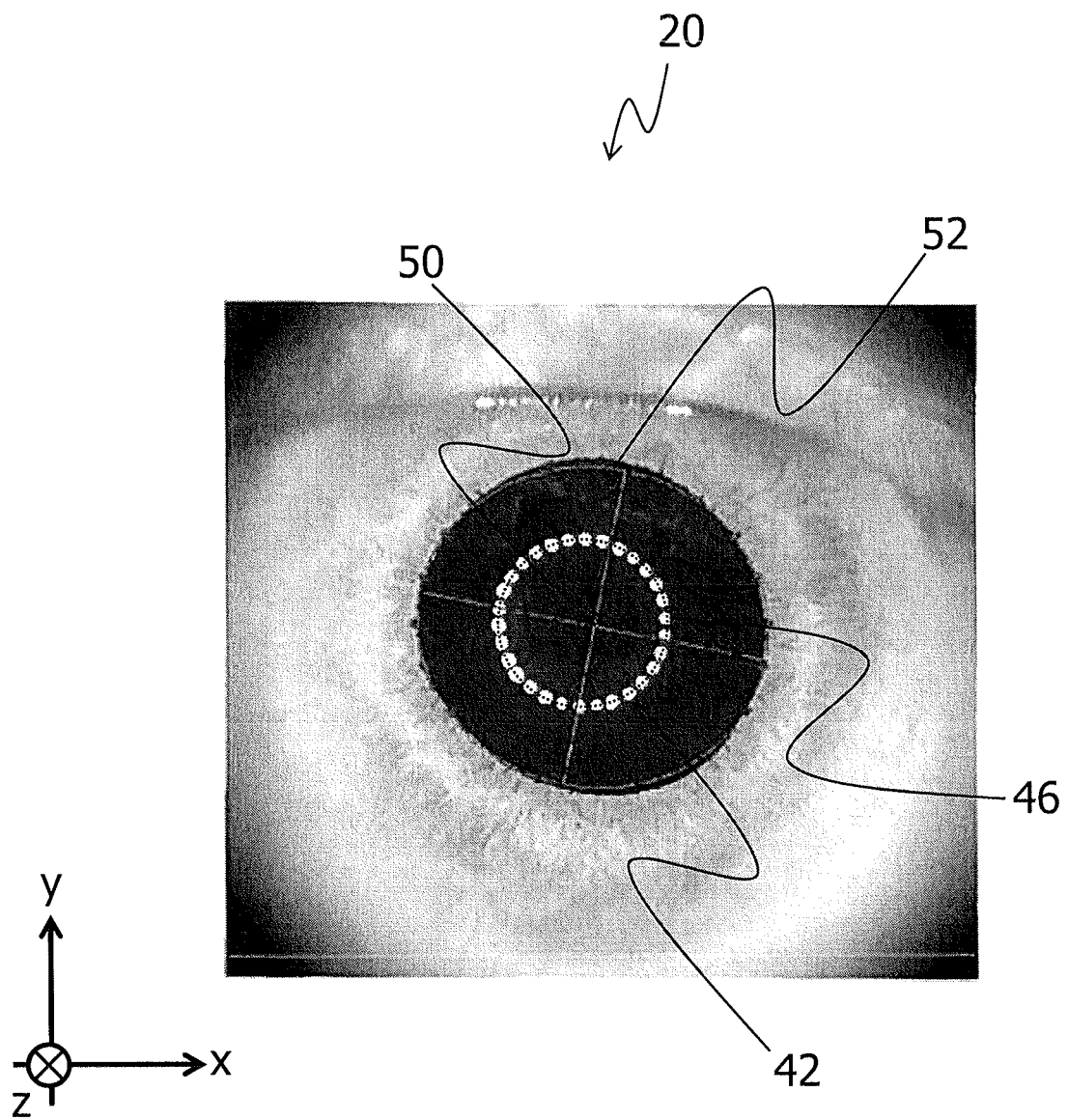
Figure 5:
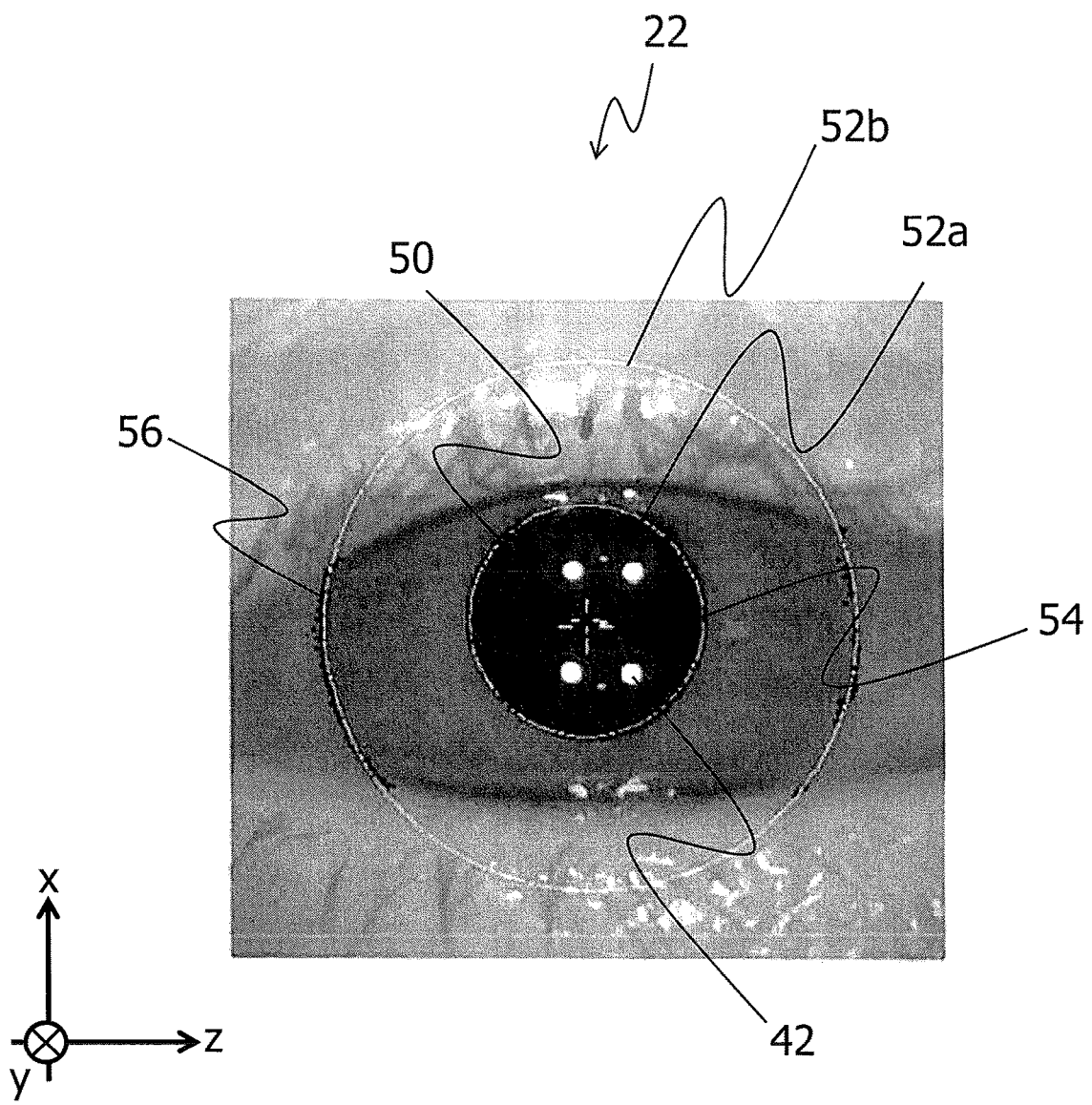

Embodiments of the present disclosure will be elucidated further in the following on the basis of the appended drawings, of which:

FIG. 1 schematically illustrates an example of a 3D tomogram representing the height profile of the front surface of a human cornea, FIG. 2 schematically illustrates an example of the height profile of FIG. 1 in a 2D representation with height contour lines, FIG. 3 schematically illustrates an embodiment of an apparatus for OCT of an eye, FIG. 4 schematically illustrates a camera image of the eye to determine movement data, FIG. 5 schematically illustrates another camera image of the eye to determine movement data.

In FIG. 1 a three-dimensional (3D) tomogram 2 of the front surface of the cornea of a human eye is schematically shown. The tomogram 2 was generated with the aid of a conventional apparatus for optical coherence tomography (OCT). To generate the 3D tomogram, a plurality of OCT images arranged in layers 4 is recorded. These single layers 4 are OCT B-scans 4 and cause the slice-like structuring of the tomogram 2. Each B-scan 4 comprises a plurality of line-like A-scans (not shown/not resolvable in FIG. 1). The tomogram 2 of FIG. 1 consists of 500×500 A-scans, wherein a single B-scan 4 consists of 500 of these A-scans.

FIG. 1 shows two different artifacts: First, as can be seen in the left and in the right part of the image, single spikes 6 represent single B-scans 6 drastically shifted in the direction of z. These spikes 6 are induced by incorrect segmentation. These artifacts 6, however, are not induced by movement of the eye. The second kind of artifacts is shown in the middle part of the image and, in this example, is represented by two groups of about three or four B-scans each that are commonly shifted slightly in the opposite direction of z. These artifacts 8 are induced by movement of the eye during the acquisition of the multiple B-scans 4 of the tomogram 2.

The movement induced artifacts 8 can also be seen in FIG. 2, which shows a 2D representation 10 of the 3D tomogram 2 shown in FIG. 1. These artifacts 8 result in a deviation of the ideally circular shaped contour of height lines 12. The movement induced artifacts 8 reduce the quality of the tomograms 2, 10 as the geometry, the contour and the height profile of the cornea are reproduced in the tomograms 2, 10 in a less qualitatively way that does not reflect the reality.

To enable 2D and/or 3D tomograms of improved quality, an apparatus 14 for OCT of an eye 16 comprises a camera system 18, see FIG. 3. The camera system 18 captures time-resolved camera images 20, 22 of the eye 16. In FIGS. 4 and 5, examples of single camera images 20, 22 are shown representing one particular time moment. The camera system 18 is connected to a control unit 24 of the apparatus 14 to transmit the camera images 20, 22 to the control unit 24 for image processing, see FIG. 3.

The apparatus 14 further comprises an OCT image-acquisition unit 26 that acquires time-resolved OCT images 28 such as B-scans 4 of the eye 16, compare FIGS. 1, 2. The OCT image-acquisition unit 26 is connected to the control unit 24 to transmit the OCT images 28 to the control unit 24 for image processing.

A measuring axis 30 of the OCT image-acquisition unit 26 and a measuring axis 32 of the camera system 18 are aligned along a common measuring axis 34 of the apparatus 14 using a beam splitter 36. The measuring axis 32 of the camera system 18 is the optical axis of one or more cameras comprised in the camera system 18. The measuring axis 30 of the OCT image-acquisition unit 26 is the propagation direction of the sampling light beam in the sample arm of the OCT image-acquisition unit 26. The common measuring axis 34 may be the optical axis defined by a scanning objective 38 of the OCT image-acquisition unit 26. The beam splitter 36 is a band pass mirror that only reflects a frequency band, in which the frequency of the light of the OCT acquisition unit falls, and else is substantially transparent for light such that the camera system 18 can image the eye 16 through beam splitter 36 and the scanning objective 38. Of course, components 18 and 26 may also be interchanged such that light for the camera system 18 is reflected at the beam splitter 36 and light for the OCT image-acquisition unit 26 is transmitted through the beam splitter 36.

The control unit 24 determines from the time-resolved camera images 20, 22 time-resolved movement data representing a movement of the eye 16 relative to the common measuring axis 34 of the apparatus 14. The time-resolved movement data allows the reconstruction of the spatial position and orientation of the eye 16 in a time-resolved manner relative to the position and orientation of the apparatus 14. As the OCT images 28 are also acquired in a time-resolved manner, each of the OCT images 28 can be associated with a corresponding spatial position and orientation of the eye. On basis of the movement data, the control unit 24 transforms at least a fraction of the OCT images 28. For example, OCT images 28 that would lead to a movement induced artifact 8 in a tomogram 2, 10 are transformed such that the movement of the eye 16 is compensated. Then the control unit 24 generates a 2D and/or 3D tomogram of the eye 16 from the OCT images 28. By this image processing, artifacts such as indicated by 8 in FIGS. 1 and 2 can be prevented.

The apparatus 14 further comprises a plurality of spot lights 40 (only two of which are shown in FIG. 3). The spot lights are LEDs and are arranged laterally shifted from the measuring axis 34 in the vicinity of the scanning objective 38. The spot lights 40 illuminate the cornea 44 of the eye 16 such that the time-resolved camera images 20, 22 show for each spot light 40 a light mark 42, see FIGS. 4 and 5. The spot lights 40 may be arranged in a circular pattern around the common measuring axis 34 and the scanning objective 38 such that the time-resolved camera images 20 show a plurality of light marks 42 in a circular-like pattern, see FIG. 4. Additionally or alternatively, two pairs of spot lights 40 may be arranged in a rectangular pattern around the common measuring axis 34 and the scanning objective 38 such that the time-resolved camera images 22 shows a plurality of light marks 42 in a rectangular-like pattern, see FIG. 5.

The control unit 24 then determines as movement data a time-resolved spatial position of two light marks 42 diametrically facing each other in the circular-like and/or rectangular-like pattern in the camera image 20, 22, see FIGS. 4 and 5, respectively. A spatial distance between these two positions is then calculated by the control unit 24. This spatial distance changes with an axial translation of the eye 16 when moving along the common measuring axis 34 (i.e. along z). The control unit 24 is calibrated such that for any spatial distance between the two light marks 42 a corresponding axial (z) translation of the eye 16 relative to the apparatus 14 can be assigned. This allows a precise time-resolved axial (z) tracking of the position and the movement of the eye 16 and thus a correction of the OCT images 28 free from axial (z) translations induced artifacts.

Additionally or alternatively, the control unit 24 may be configured to determine as movement data a time-resolved spatial size of a circle 46 (the dotted line in FIG. 4) and/or of a rectangle (compare FIG. 5) fitted to the plurality of light marks 42 shown in the camera images 20. This corresponds to a simultaneous determining of spatial distances between two light marks 42 for multiple pairs of light marks 42. The control unit 24 may be calibrated such that for any spatial size a corresponding axial (z) translation of the eye 16 relative to the apparatus 14 can be assigned. This allows an even more precise time-resolved axial (z) tracking of the position and the movement of the eye 16 and thus an improved correction of the OCT images 28 free from axial (z) translations induced artifacts.

The control unit 24 also determines from the OCT images 28 curvature values representing the curvature of the outer surface 48 of the cornea 44. This allows the determining of the curvature along the meridians of the outer surface 48 of the cornea 44 and thus a more precise calibration of the control unit 24 for assigning the axial (z) translation of the eye 16 relative to the apparatus 14.

The control unit 24 also determines as movement data a time-resolved position of a reference point 50, 50a, 50b being the center of a circle 52, 52a, 52b and/or of a circle-like form fitted to the pupil 54 of the eye 16 and/or to an outer edge of the iris 56 of the eye 16, see FIGS. 4 and 5. In FIG. 4, for example, a circle 52 is fitted to the pupil. In FIG. 5, there are determined two reference points 50a, 50b shown as two cross-hairs being the center of two circles 52a, 52b, one circle 52a fitted to the pupil 54, another circle 52b fitted to edge of the iris 56. This allows a time-resolved lateral (x, y) tracking of the position and movement of the eye 16 and thus a correction of the OCT images 28 free from lateral (x, y) translations induced artifacts.

Further, the control unit determines as movement data a time-resolved position of an eye feature being an extended feature of the iris 56 of the eye 16 and/or of a vessel structure in the sclera of the eye 16 (not shown). This allows a time-resolved rotational (i.e. cyclotorsional) tracking of the position and movement of the eye 16 and thus a correction of the OCT images free from rotations (cyclotorsions) induced artifacts.

The camera system 18 captures the time-resolved camera images 20, 22 with a camera imaging rate. The OCT image-acquisition unit 26 acquires time-resolved OCT images 28 with an OCT imaging rate. The control unit 24 controls the camera imaging rate and the OCT imaging rate.

In one setting, the camera imaging rate substantially equals the OCT imaging rate, for example, by synchronizing the camera imaging rate and the OCT imaging rate. This allows assigning a single camera image 20, 22 to each OCT image 28 and thus a time-adapted correction of the OCT images 28 free from movement artifacts. In an alternative setting, the camera imaging rate is lower than the OCT imaging rate. This allows assigning a single camera image 20, 22 to multiple different OCT images 28, thus a less time-consuming determining of the movement data and therefore a faster generation of tomograms 2, 10. In still another alternative setting, the camera imaging rate is higher than the OCT imaging rate. This allows assigning multiple camera images 20, 22 to each OCT image 28 enabling a highly time-resolved correction of the OCT images on an A-scan basis.

The invention claimed is:

1. An apparatus for optical coherence tomography (OCT) of an eye, comprising:
   a camera system configured to capture time-resolved camera images of the eye;
   an OCT image-acquisition unit configured to acquire time-resolved OCT images of the eye, wherein a measuring axis of the OCT image-acquisition unit and a measuring axis of the camera system are aligned along a common measuring axis of the apparatus using a beam splitter;
   a control unit configured to:
      determine, from the time-resolved camera images, time-resolved movement data representing a movement of the eye relative to the measuring axis of the apparatus;
      transform at least a fraction of the OCT images on basis of the movement data; and
      generate a tomogram of the eye from the OCT images; and
   a plurality of spot lights arranged in a spot light geometrical pattern around the measuring axis of the apparatus, the spot lights being configured to:
      illuminate the cornea of the eye such that the time-resolved camera images comprise a plurality of light marks in a light mark geometrical pattern; and
      determine, as movement data, a time-resolved spatial size of a geometrical pattern fitted to the plurality of light marks;
   wherein the control unit is calibrated such that for each spatial size of the geometrical pattern fitted to the light marks a corresponding axial translation of the eye relative to the apparatus is assigned.

2. The apparatus according to claim 1, wherein the apparatus further comprises a cornea contour determining unit being configured to determine curvature values representing the curvature of the outer surface of the cornea of the eye.

3. The apparatus according to claim 1, wherein the control unit is further configured to determine curvature values from the OCT images, the curvature values representing the curvature of the outer cornea surface of the eye.

4. The apparatus according to claim 1, wherein the control unit is further configured to determine, as movement data, a time-resolved spatial position of a reference point being at least one of:
the center of a geometrical pattern fitted to the pupil of the eye and/or to an outer edge of the iris of the eye; and
the center of a geometrical pattern fitted to the light marks.

5. The apparatus according to claim 1, wherein the control unit is further configured to determine, as movement data, a time-resolved spatial position of an eye feature being an extended feature of the iris of the eye or of a vessel structure in the sclera of the eye.

6. The apparatus according to claim 1, wherein the camera system is configured to capture time-resolved camera images with a camera imaging rate and the OCT image-acquisition unit is configured to acquire time-resolved OCT images with an OCT imaging rate, and wherein the camera imaging rate substantially equals the OCT imaging rate, or the camera imaging rate is higher than the OCT imaging rate, or the camera imaging rate is lower than the OCT imaging rate.

7. The apparatus according to claim 1, wherein the camera system comprises only a single camera.

8. A method for optical coherence tomography (OCT) of an eye, comprising:
capturing time-resolved camera images of the eye using a camera system;
acquiring time-resolved OCT images of the eye using an OCT image-acquisition unit, wherein a measuring axis of the OCT image-acquisition unit and a measuring axis of the camera system are aligned along a common measuring axis using a beam splitter;
determning, from the time-resolved camera images, time-resolved movement data representing a movement of the eye relative to the measuring axis using a control unit;
transforming at least a fraction of the OCT images on basis of the movement data using the control unit; and
generating a tomogram of the eye from the OCT images using the control unit;
the method further comprising:
illuminating the cornea of the eye using a plurality of spot lights arranged in a spot light geometrical pattern around the measuring axis such that the time-resolved camera images comprise a plurality of light marks in a light mark geometrical pattern;
determining, as movement data, a time-resolved spatial size of a geometrical pattern fitted to the plurality of light marks using the control unit; and
assigning for each spatial size of the geometrical pattern fitted to the light marks a corresponding axial translation of the eye relative to the apparatus using the control unit.

9. The method according to claim 8, further comprising:
determining curvature values representing the curvature of the outer cornea surface of the eye using a cornea contour determining unit.

10. The method according to claim 8, further comprising:
determining from the OCT images curvature values representing the curvature of the outer surface of the cornea of the eye by use the control unit.

11. The method according to claim 8, further comprising:
determining, as movement data, a time-resolved spatial position of a reference point being at least one of:
the center of a geometrical pattern fitted to the pupil of the eye and/or to an outer edge of the iris of the eye; and
the center of a geometrical pattern fitted to the light marks using the control unit.

12. The method according to claim 8, further comprising:
determining, as movement data, a time-resolved position of an eye feature being an extended feature of the iris of the eye or of a vessel structure in the sclera of the eye using the control unit.

13. The method according to claim 8, further comprising:
capturing time-resolved camera images with a camera imaging rate and acquiring time-resolved OCT images with a OCT imaging rate, wherein the camera imaging rate substantially equals the OCT imaging rate, or the camera imaging rate is higher than the OCT imaging rate, or the camera imaging rate is lower than the OCT imaging rate.

* * * * *